(12) United States Patent
Egashira et al.

(10) Patent No.: US 7,309,693 B2
(45) Date of Patent: Dec. 18, 2007

(54) PREVENTIVES AND REMEDIES FOR PULMONARY HYPERTENSION

(75) Inventors: Kensuke Egashira, Fukuoka (JP); Yoshikazu Yonemitsu, Fukuoka (JP); Katsuo Sueishi, Fukuoka (JP); Yasuhiro Ikeda, Fukuoka (JP); Yoshiyuki Inada, Kawanishi (JP)

(73) Assignees: Kensuke Egashira, Fukuoka (JP); Takeda Chemical Industries Ltd., Osaka (JP)

( * ) Notice: Subject to any disclaimer, the term of this patent is extended or adjusted under 35 U.S.C. 154(b) by 585 days.

(21) Appl. No.: 10/276,971

(22) PCT Filed: May 25, 2001

(86) PCT No.: PCT/JP01/04381

§ 371 (c)(1), (2), (4) Date: Mar. 22, 2003

(87) PCT Pub. No.: WO01/89582

PCT Pub. Date: Nov. 29, 2001

(65) Prior Publication Data

US 2003/0162737 A1 Aug. 28, 2003

(30) Foreign Application Priority Data

May 26, 2000 (JP) ............................ 2000-161145

(51) Int. Cl.
- *A61K 31/70* (2006.01)
- *A01N 43/04* (2006.01)
- *C12P 19/34* (2006.01)
- *C07H 21/02* (2006.01)
- *C07H 21/04* (2006.01)

(52) U.S. Cl. ................. 514/44; 435/91.1; 536/23.1
(58) Field of Classification Search ................. 514/44; 435/91.1; 536/23.1
See application file for complete search history.

(56) References Cited

U.S. PATENT DOCUMENTS

| | | | |
|---|---|---|---|
| 5,459,128 A | 10/1995 | Rollins et al. | 514/8 |
| 5,705,360 A | 1/1998 | Rollins et al. | 435/69.1 |
| 6,133,502 A * | 10/2000 | Kasuga et al. | 800/14 |
| 6,451,842 B1 * | 9/2002 | Shiota et al. | 514/422 |
| 2004/0185450 A1 * | 9/2004 | Heavner et al. | 435/6 |
| 2005/0232923 A1 * | 10/2005 | Yan et al. | 424/146.1 |

FOREIGN PATENT DOCUMENTS

| | | | |
|---|---|---|---|
| EP | 0887081 | | 12/1998 |
| JP | 11-049700 | | 2/1999 |
| JP | 2000-161145 | * | 5/2000 |
| WO | WO 95/13295 | | 5/1995 |
| WO | WO 98/39434 | | 9/1998 |

OTHER PUBLICATIONS

Kasahara et al., MCAF/MCP-1 protein expression in a rat model for pulmonary hypertension induced by monocrotaline. Chest 114(1 Suppl):67S, 1998.*
Zhang and Rollins, A dominant negative inhibitor indicates that monocyte chemoattractant protein 1 functions as a dimer. Mol Cell Biol. 15(9):4851-5, 1995.*
Ikeda et al., Anti-monocyte chemoattractant protein-1 gene therapy attenuates pulmonary hypertension in rats. Am J Physiol Heart Circ Physiol. 283(5): H2021-8, 2002.*
Kimura, et al. "Analysis of Monocyte Chemotactic and Activating Factor (MCAF/MCP-1) in Rats with Experimental Pulmonary Hypertension and Anti-MCAF Antibody Therapy" 151-155 (1998) (with Full Translation).
Matsushima, et al. "Treatment of Immunologic and Inflammatory diseases Using a Cytokine/Chemokine As A Molecular Target" 100-101(1998) Partial Translation.
Kimura, et al. "Alleviation of Monocrotaline-Induced Pulmonary Hypertension by Antibodies to Monocyte Chemotactic and Activating Factor/Monocyte Chemoattractant Protein-1" Lab. Invest. 78(5): 571-581(1998).
B. Rollins "Monocyte chemoattractant protein 1: a potential regulator of monocyte recruitment in inflammatory disease" Molecular Medicine Today 198-204 (May 1996).

* cited by examiner

*Primary Examiner*—Valarie Bertoglio
*Assistant Examiner*—Wu-Cheng Winston Shen
(74) *Attorney, Agent, or Firm*—Hogan & Hartson LLP

(57) ABSTRACT

The present invention provides a prophylactic and/or therapeutic agent for pulmonary hypertension, comprising an antagonistic mutein of MCP-1 or a salt thereof, a DNA molecule comprising a nucleotide sequence encoding the antagonistic mutein of MCP-1, or a neutralizing antibody against MCP-1. The antagonistic mutein of MCP-1 or a salt thereof, the DNA molecule having a nucleotide sequence encoding the antagonistic mutein of MCP-1, or the neutralizing antibody against MCP-1 has hypotensive activity, and thus is useful as a pharmaceutical agent for preventing and/or treating pulmonary hypertension (primary pulmonary hypertension, in particular).

4 Claims, No Drawings

PREVENTIVES AND REMEDIES FOR PULMONARY HYPERTENSION

FIELD OF THE INVENTION

The present invention relates to novel prophylactic and/or therapeutic agents for pulmonary hypertension.

BACKGROUND ART

MPC-1 (Monocyte chemoattractant protein-1: macrophage chemotactic factor) is a member of the C—C chemokine family and is known to be highly expressed in the arteriosclerotic (e.g. atherosclerotic) lesion (Takeya, M. et al., Hum. Pathol. 24: 534-539 (1993); Yla-Herttuala, S. et al., Proc. Natl. Acad. Sci. USA, 88: 5252-5257 (1991)).

On the other hand, primary pulmonary hypertension (PH) is a disease with poor prognosis, and heart-lung transplantation is the only therapy for this disease at present. However, heart-lung transplantation has considerable difficulty being used as a practical treatment due to the limited supply of donors.

DISCLOSURE OF THE INVENTION

In the view of the situation described above, development of a therapeutic agent that enables treatment of pulmonary hypertension (particularly, primary pulmonary hypertension) without performing heart-lung transplantation has been expected.

MPC-1 (Monocyte chemoattractant protein-1: macrophage chemotactic factor) is a member of the C—C chemokine family and is known to be highly expressed in the arteriosclerotic (e.g. atherosclerotic) lesion (Takeya, M. et al., Hum. Pathol. 24: 534-539 (1993); Yla-Herttuala, S. et al., Proc. Natl. Acad. Sci. USA, 88: 5252-5257 (1991)).

On the other hand, in the course of primary pulmonary hypertension, inflammation of pulmonary arterioles (inflammatory response mainly involving monocytes/macrophages) develops, and then increase of pulmonary vascular resistance due to hypertrophy of tunica media, and also right ventricle hypertrophy follow. The present inventors discovered that an antagonistic mutein of MCP-1 ("antagonistic mutein" may be used herein as a synonym of "dominant negative mutein or mutant") and the like, which have an inhibitory effect on MCP-1 function as described above, are unexpectedly useful as a prophylactic or therapeutic agent for primary pulmonary hypertension. They further pursued this study and have completed the invention.

The present invention relates to:

(1) A prophylactic and/or therapeutic agent for pulmonary hypertension, comprising an antagonistic mutein of MCP-1 or a salt thereof, a DNA molecule having a nucleotide sequence encoding the antagonistic mutein of MCP-1, or a neutralizing antibody against MCP-1;

(2) The agent described in (1), wherein said antagonistic mutein of MCP-1 is 7ND-MCP-1;

(3) The agent described in (1), wherein said pulmonary hypertension is primary pulmonary hypertension;

(4) Use of the antagonistic mutein of MCP-1 or a salt thereof, a DNA molecule having a nucleotide sequence encoding the antagonistic mutein of MCP-1, or a neutralizing antibody against MCP-1 described in (1) for producing a prophylactic and/or therapeutic agent for pulmonary hypertension; and (5) A method for preventing and/or treating pulmonary hypertension, comprising administration of the antagonistic mutein of MCP-1 or a salt thereof, or a nucleotide sequence encoding the antagonistic mutein of MCP-1 described in (1) to mammals.

The antagonistic mutein of MCP-1 of the present invention (hereinafter may be referred only to as "the muteins of the invention") may be any mutein that has an inhibitory effect on the function (e.g. monocyte/macrophage chemotactic (migration) function) of MCP-1 (Rollins, B. J., Chemokines. Blood. 90: 909-928 (1997); a protein consisting of the amino acid sequence set forth in SEQ ID NO: 1). Specifically, they include:

(1) A mutein consisting of the partial amino acid sequence corresponding to the residues 2-76 from the N-terminus of MCP-1;

(2) A mutein consisting of the partial amino acid sequence corresponding to the residues 3-76 from the N-terminus of MCP-1;

(3) A mutein consisting of the partial amino acid sequence corresponding to the residues 4-76 from the N-terminus of MCP-1;

(4) A mutein consisting of the partial amino acid sequence corresponding to the residues 5-76 from the N-terminus f MCP-1;

(5) A mutein consisting of the partial amino acid sequence corresponding to the residues 6-76 from the N-terminus of MCP-1;

(6) A mutein consisting of the partial amino acid sequence corresponding to the residues 7-76 from the N-terminus of MCP-1;

(7) A mutein consisting of the partial amino acid sequence corresponding to the residues 8-76 from the N-terminus of MCP-1;

(8) A mutein consisting of the partial amino acid sequence corresponding to the residues 9-76 from the N-terminus of MCP-1;

(9) A mutein consisting of the partial amino acid sequence corresponding to the residues 10-76 from the N-terminus of MCP-1;

(10) A mutein consisting of the partial amino acid sequence corresponding to the residues 11-76 from the N-terminus of MCP-1;

(11) A mutein consisting of the amino acid sequence in which the residues 2-8 from the N-terminus of MCP-1 are deleted (SEQ ID NO: 2) (hereinafter referred to as "7ND-MCP-1");

(12) A mutein in which Asp, the third residue from the N-terminus of MCP-1, is replaced with Ala;

(13) A mutein in which Val, the 22nd residue from the N-terminus of MCP-1, is replaced with Asp; and

(14) A mutein in which Arg, the 24th residue from the N-terminus of MCP-1, is replaced with Leu.

In particular, 7ND-MCP-1 is preferabley used.

The mutein of the present invention may be a mutein of protein derived from any cells (e.g., retina cells, liver cells, splenocytes, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophage, T cells, B cells, natural killer cells, mast cells, neutrophil, basophil, eosinophil, monocyte), megakaryocyte, synovial cells, chondrocytes, bone cells, osteoblasts, osteoclasts, mammary gland cells, hepatocytes or interstitial cells, the corresponding precursor cells, stem cells, cancer cells, etc.), or any tissues where such cells are present, e.g., brain or any region of the brain (e.g., olfactory bulb, amygdaloid nucleus, basal ganglia, hippocampus, thalamus, hypothalamus, subthalamic nucleus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine, small intestine, intestine duodenum), blood vessel, heart, thymus, spleen, submandibular gland, peripheral blood, peripheral blood cells, prostate, testis, ovary, placenta, uterus, bone, joint, skeletal muscle, etc. from human and other mammalians (e.g., guinea pigs, rats, mice, rabbits, swine, sheep, bovine, monkeys, etc.). The mutein may also be a synthetic protein.

The mutein of the present invention may have substantially the same amino acid sequence as that shown by SEQ ID NO: 2 as long as it can inhibit the activity of MCP-1 (for example, macrophage chemotactic activity). The substantially same amino acid sequence as that shown by SEQ ID NO: 2 includes, for example, amino acid sequences having about 40% or more, preferably about 60% or more, more preferably about 80% or more, further preferably about 90% or more, most preferably about 95% or more homology with the amino acid sequence shown by SEQ ID NO: 2.

The mutein of the present invention also includes a mutein comprising (i) an amino acid sequence having deletion of 1 or more (preferably 1 to about 20, more preferably 1 to about 9, further preferably several (1 to 5)) amino acids in the amino acid sequence shown by SEQ ID NO: 2, (ii) an amino acid sequence having addition of 1 or more (preferably 1 to about 20, more preferably 1 to about 9, further preferably several (1 to 5)) amino acids in the amino acid sequence shown by SEQ ID NO: 2, (iii) an amino acid sequence having substitution of 1 or more (preferably 1 to about 20, more preferably 1 to about 9, further preferably several (1 to 5)) amino acids with other amino acids in the amino acid sequence shown by SEQ ID NO: 2, or (iv) an amino acid sequence having a combination of the above modifications. When the amino acid sequence is modified via addition or deletion of amino acid residues, positions for the addition or deletion are not specifically limited.

The muteins of the present invention are represented in accordance with the conventional way of describing peptides, with the N-terminus (amino terminus) on the left side and the C-terminus (carboxyl terminus) on the right side. In the muteins of the present invention, including the mutein consisting of the amino acid sequence shown by SEQ ID NO:2, the C-terminus is usually in the form of a carboxyl group (—COOH) or a carboxylate (—COO⁻) but may be in the form of an amide (—CONH$_2$) or an ester (—COOR).

Examples of the ester group shown by R include a $C_{1-6}$alkyl group such as methyl, ethyl, n-propyl, isopropyl, n-butyl, etc.; a $C_{3-8}$cycloalkyl group such as cyclopentyl, cyclohexyl, etc.; a $C_{6-12}$ aryl group such as phenyl, α-naphthyl, etc.; a $C_{7-14}$ aralkyl group such as a phenyl-$C_{1-2}$-alkyl group, e.g., benzyl, phenethyl, etc., or an α-naphthyl-$C_{1-2}$-alkyl group such as α-naphthylmethyl, etc.; and the like. In addition, pivaloyloxymethyl or the like, which is used widely as an ester for oral administration, may also be used.

When the mutein of the present invention contains a carboxyl group (or a carboxylate) at a position other than the C-terminus, it may be amidated or esterified and such an amide or ester is also included within the mutein of the present invention. The ester group may be the same group as that described with respect to the C-terminus described above.

Furthermore, the muteins of the present invention include variants of the above-mentioned muteins, wherein the amino group at the N-terminal methionine residue of the mutein supra is protected with a protecting group (for example, a $C_{1-6}$ acyl group such as a $C_{2-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated proteins such as glycoproteins bound to sugar chains.

A salt of the mutein of the present invention is a physiologically acceptable salt with an acid or base. Especially, a physiologically acceptable acid addition salt is preferred. Examples of the salt include, for example, a salt with an inorganic acid (e.g., hydrochloric acid, phosphoric acid, hydrobromic acid, sulfuric acid) or with an organic acid (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid).

The mutein of the present invention or a salt thereof may be produced by preparing MCP-1 via a known purification method from human or other mammalian cells or tissues as described above, and then deleting an amino acid residue or a partial amino acid sequence from MCP-1 in accordance with a known method; or by culturing a transformant having a DNA encoding the mutein of the present invention, as later described. Furthermore, the mutein or its salt may also be produced by a method for protein synthesis as described below or a modified method thereof.

When MCP-1 is produced from human or mammalian tissues or cells, after homogenization of human or mammalian tissues or cells, extraction with an acid or the like, and isolation and purification by a combination of chromatography techniques such as reverse phase chromatography, ion exchange chromatography, and the like are carried out.

To synthesize the mutein of the present invention, commercially available resins that are used for protein synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmehtylphenyl acetamidomethyl resin, polyacrylamide resin, 4-(2',4'-dimethoxyphenylhydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective mutein according to various condensation methods publicly known in the art. At the end of the reaction, the mutein is cut out from the resin and at the same time, the protecting groups are removed. Then, intramolecular disulfide bond-forming reaction is performed in a highly diluted solution to obtain the objective mutein or its amides.

For condensation of the protected amino acids described above, a variety of activation reagents for protein synthesis may be used, and carbodiimides are particularly preferable. Examples of such carbodiimides include DCC, N,N'-diisopropylcarbodiimide, N-ethyl-N'-(3-dimethylaminoprolyl) carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents known to be usable for protein condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitrites such as acetonitrile, propionitrile, etc.; esters such as methyl acetate, ethyl acetate, etc.; and appropriate mixtures of these solvents. The reaction temperature is appropriately chosen from the range known to be applicable to protein binding reactions and is usually selected in the range of approximately −20° C. to 50° C. The activated amino acid derivatives are used generally in an excess of 1.5 to 4 times. The condensation is examined by a test using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to avoid adverse effect on the subsequent reaction.

Examples of the protecting groups used to protect the amino groups of the starting compounds include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower alkanoyl group, such as acetyl group, an aroyl group such as benzoyl group, and a group derived from carbonic acid such as benzyloxycarbonyl group, ethoxycarbonyl group, etc. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting compounds include the corresponding acid anhydrides, azides, activated esters (esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)). As the activated amino acids, in which the amino groups are activated in the starting material, the corresponding phosphoric amides are employed.

To eliminate (remove) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethane-sulfonic acid or trifluoroacetic acid, or a mixture solution of these acids; a treatment with a base such as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol or 1,4-butanedithiol, as well as by a treatment with an alkali such as a dilute sodium hydroxide solution and dilute ammonia.

Protection of functional groups that should not be involved in the reaction of the starting materials, protecting groups, elimination of the protecting groups and activation of functional groups involved in the reaction may be appropriately selected from known groups and known means.

In another method for obtaining an amide of the mutein, for example, the α-carboxyl group of the carboxy terminal amino acid is first protected by amidation; the peptide (protein) chain is then extended from the amino group side to a desired length. Thereafter, a protein in which only the protecting group of the N-terminal α-amino group in the peptide chain has been eliminated from the protein and a protein in which only the protecting group of the C-terminal carboxyl group has been eliminated are prepared. The two proteins are condensed in a mixture of the solvents described above. The details of the condensation reaction are the same as described above. After the protected protein obtained by the condensation is purified, all the protecting groups are eliminated by the method described above to give the desired crude protein. This crude protein is purified by various known purification means. Lyophilization of the major fraction gives an amide of the desired mutein.

To prepare an ester of the mutein, for example, the α-carboxyl group of the carboxy terminal amino acid is condensed with a desired alcohol to prepare the amino acid ester, which is followed by procedure similar to the preparation of the amidated mutein above to give an ester form of the desired mutein.

The mutein of the present invention can be produced by a known method for peptide synthesis, or by cleaving MCP-1 with an appropriate peptidase. For the method for peptide synthesis, for example, either solid phase synthesis or liquid phase synthesis may be used. That is, a partial peptide or an amino acid that can compose the mutein of the present invention is condensed with the remaining part. When the product contains protecting groups, these protecting groups are removed to give the desired mutein. Publicly known methods for condensation and elimination of the protecting groups are described in 1)-5) below.

1) M. Bodanszky & M. A. Ondetti: Peptide Synthesis, Interscience Publishers, New York (1966)

2) Schroeder & Luebke: The Peptide, Academic Press, New York (1965)

3) Nobuo Izumiya, et al.: *Peptide Gosei-no-Kiso to Jikken* (Basics and experiments of peptide synthesis), published by Maruzen Co. (1975)

4) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)

5) Haruaki Yajima, ed.: *Zoku Iyakuhin no Kaihatsu* (A sequel to Development of Pharmaceuticals), Vol. 14, Peptide Synthesis, published by Hirokawa Shoten After completion of the reaction, the mutein of the present invention may be purified and isolated by a combination of conventional purification methods such as solvent extraction, distillation, column chromatography, liquid chromatography and recrystallization. When the mutein obtained by the above method is in a free form, the mutein can be converted into an appropriate salt by a publicly known method; when the mutein is obtained in a salt form, it can be converted into a free form by a publicly known method.

The DNA encoding the mutein of the present invention may be any DNA containing a nucleotide sequence encoding the mutein, and may also be derived from any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

Specifically, the DNA encoding MCP-1 consisting of the amino acid sequence shown by SEQ ID NO: 1 includes a DNA having the nucleotide sequence shown by SEQ ID NO: 3. The DNA encoding 7ND-MCP-1 consisting of the amino acid sequence shown by SEQ ID NO: 2 includes a DNA having the nucleotide sequence shown by SEQ ID NO: 4.

For cloning of the DNA that encodes the mutein of the present invention, the DNA may be either amplified by PCR using synthetic DNA primers containing a part of the nucleic acid sequence encoding the mutein of the present invention, or the DNA inserted into an appropriate vector can be selected by hybridization with a labeled DNA fragment or a labeled synthetic DNA that encodes a part or entire region of the mutein of the present invention. The hybridization can be carried out, for example, according to the method described in Molecular Cloning, 2nd, J. Sambrook et al., Cold Spring Harbor Lab. Press, 1989. The hybridization may also be performed using a commercially available library in accordance with the protocol described in the attached instruction.

Modification (deletion, addition, substitution) of the DNA sequence can be effected in accordance with a publicly known method such as the Gupped duplex method or the Kunkel method or its modification, using a publicly known kit available as Mutan™-G or Mutan™-K (Takara Shuzo Co., Ltd.).

The cloned DNA encoding the mutein of the present invention can be used depending upon its purpose, as it is or if desired, after digestion with a restriction enzyme or after addition of a linker thereto. The DNA may contain ATG as a translation initiation codon at the 5' end thereof and may further contain TAA, TGA or TAG as a translation termination codon at the 3' end thereof. These translation initiation and termination codons may also be added by using an appropriate synthetic DNA adapter.

The expression vector for the mutein of the present invention can be produced, for example, by (a) excising the desired DNA fragment from the DNA encoding the mutein of the present invention, and then (b) ligating the DNA fragment downstream of a promoter in an appropriate expression vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ-phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter suitable for a host to be used for gene expression. In the case of using animal cells as the host, examples of the promoter include SRα promoter, SV40 promoter, LTR promoter, CMV promoter, HSV-TK promoter, etc. Among them, CMV promoter or SRα promoter is preferably used. When the host is bacteria of the genus Escherichia, preferred examples of the promoter include trp promoter, lac promoter, recA promoter, $\lambda P_L$ promoter, lpp promoter, etc. In the case of using bacteria of the genus *Bacillus* as the host, preferred example of the promoter are SPO1 promoter, SPO2 promoter and penP promoter. When yeast is used as the host, preferred examples of the promoter are PHO5 promoter, PGK promoter, GAP promoter and ADH promoter. When insect cells are used as the host, preferred examples of the promoter include polyhedrin prompter and P10 promoter.

In addition to the foregoing examples, the expression vector may further optionally contain an enhancer, a splicing signal, a poly A addition signal, a selection marker, SV40 replication origin (hereinafter sometimes abbreviated as SV40ori) etc. Examples of the selection marker include dihydrofolate reductase (hereinafter sometimes abbreviated as dhfr) gene, ampicillin resistant gene (hereinafter sometimes abbreviated as $Amp^r$), neomycin resistant gene (hereinafter sometimes abbreviated as $Neo^r$, G418 resistance), etc. The dhfr gene confers methotrexate (MTX) resistance and Neo gene confers G418 resistance. In particular, when dhfr gene is used as the selection marker in $dhfr^-$ Chinese Hamster Ovary (CHO) cells, the target gene can also be selected in a thymidine-free medium.

If necessary and desired, a signal sequence that matches with a host is added to the N-terminus of the mutein of the present invention. Examples of the signal sequence that can be used are Pho A signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector containing the DNA encoding the mutein of the present invention thus constructed, a transformant can be manufactured.

Examples of the host, which may be employed, are bacteria belonging to the genus *Escherichia*, bacteria belonging to the genus *Bacillus*, yeast, insect cells, insects and animal cells, etc.

Specific examples of the bacteria belonging to the genus *Escherichia* include *Escherichia coli* K12 DH1 (Proc. Natl. Acad. Sci. U.S.A., 60, 160 (1968)), JM103 (Nucleic Acids Research, 9, 309 (1981)), JA221 (Journal of Molecular Biology, 120, 517 (1978)), HB101 (Journal of Molecular Biology, 41, 459 (1969)), C600 (Genetics, 39, 440 (1954)), etc.

Examples of the bacteria belonging to the genus *Bacillus* include *Bacillus subtilis* MI114 (Gene, 24, 255 (1983)), 207-21 (Journal of Biochemistry, 95, 87 (1984)), etc.

Examples of yeast include *Saccharomyces cereviseae* AH22, AH22R⁻, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cells (Sf cells), MG1 cells derived from mid-intestine of *Trichoplusia ni*, High Five™ cells derived from egg of *Trichoplusia ni*, cells derived from *Mamestra brassicae*, cells derived from *Estigmena acrea*, etc.; and for the virus BmNPV, *Bombyx mori* N cells (BmN cells), etc. are used. Examples of the Sf cell which can be used are Sf9 cells (ATCC CRL1711) and Sf21 cells (both cells are described in Vaughn, J. L. et al., In Vitro, 13 213-217 (1977).

As the insect, for example, a larva of *Bombyx mori* can be used (Maeda, et al., Nature, 315, 592 (1985)).

Examples of animal cells include monkey cells COS-7, Vero, Chinese hamster ovary cells (hereinafter referred to as CHO cells), dhfr gene-deficient Chinese hamster ovary cells (hereinafter simply referred to as CHO(dhfr⁻) cell), mouse L cells, mouse AtT-20, mouse myeloma cells, rat GH3, human FL cells, 293 cells, C127 cells, BALB3T3 cells, Sp-2 cells, etc. Among those, CHO cells, CHO (dhfr⁻) cells, 293 cells are preferred.

Bacteria belonging to the genus *Escherichia* can be transformed, for example, by the method described in Proc. Natl. Acad. Sci. U.S.A., 69, 2110 (1972) or Gene, 17, 107 (1982).

Bacteria belonging to the genus *Bacillus* can be transformed, for example, by the method described in Molecular & General Genetics, 168, 111 (1979).

Yeast can be transformed, for example, by the method described in Methods in Enzymology, 194, 182-187 (1991), Proc. Natl. Acad. Sci. U.S.A., 75, 1929 (1978), etc.

Insect cells or insects can be transformed, for example, according to the method described in Bio/Technology, 6, 47-55(1988), etc.

Animal cells can be transformed, for example, according to the method described in *Saibo Kogaku* (Cell Engineering), extra issue 8, *Shin Saibo Kogaku Jikken Protocol* (New Cell Engineering Experimental Protocol), 263-267 (1995), published by Shujunsha, or Virology, 52, 456 (1973).

The method of introducing the expression vector into cells includes, for example, calcium phosphate method (Graham, F. L. and van der Eb, A. J. Virology, 52, 456-467 (1973)), eectroporation (Nuemann, E. et al. Embo J., 1, 841-845 (1982)),etc.

Thus, a transformant transformed with the expression vector containing the DNA encoding the mutein of the present invention can be obtained.

Furthermore, to express the mutein of the present invention in a stable manner using animal cells, the animal cell clone can be selected, the chromosome of which the introduced expression vector is incorporated into. To be more specific, using the above selection marker as an index, a transformant can be selected. From these animal cells obtained by use of the selection marker, it is possible to obtain a stable animal cell strain expressing highly the mutein of the present invention by repeating the clonal selection. Moreover, when using dhfr gene as a selection marker, the cells are cultured in gradually increased concentrations of MTX, and a MTX-resistant cell strain is selected. In this way, it is possible to obtain an animal cell strain with higher expression by amplifying the DNA encoding the mutein as well as dhfr gene in the cell.

The mutein of the present invention can be produced by cultivating the above-mentioned transformant under condition capable of expressing the DNA encoding the mutein of the present invention; and producing and accumulating the mutein of the present invention.

When the host is bacteria belonging to the genus *Escherichia* or the genus *Bacillus*,the transformant can be appropriately incubated in a liquid medium which contains materials required for growth of the transformant such as carbon sources, nitrogen sources, inorganic materials, and so on. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast, vitamins, growth promoting factors etc. may also be added to the medium. Preferably, pH of the medium is adjusted to about 5 to about 8.

A preferred example of the medium for incubation of the bacteria belonging to the genus *Escherichia* is M9 medium supplemented with glucose and Casamino acids (Miller, Journal of Experiments in Molecular Genetics, 431-433, Cold Spring Harbor Laboratory, New York, 1972). If necessary and desired, a chemical such as 3β-indolylacrylic acid can be added to the medium thereby to activate the promoter efficiently.

When the bacteria belonging to the genus *Escherichia* are used as the host, the transformant is usually cultivated at about 15° C. to about 43° C. for about 3 hours to about 24 hours. If necessary and desired, the culture may be aerated or agitated.

When the bacteria belonging to the genus *Bacillus* are used as the host, the transformant is cultivated generally at about 30° C. to about 40° C. for about 6 hours to about 24 hours. If necessary and desired, the culture can be aerated or agitated.

When yeast is used as the host, the transformant is cultivated, for example, in Burkholder's minimal medium (Bostian, K. L. et al., Proc. Natl. Acad. Sci. U.S.A., 77, 4505 (1980)) or in SD medium supplemented with 0.5% Casamino acids (Bitter, G. A. et al., Proc. Natl. Acad. Sci. U.S.A., 81, 5330 (1984)). Preferably, pH of the medium is adjusted to about 5 to about 8. In general, the transformant is cultivated at about 20° C. to about 35° C. for about 24 hours to about 72 hours. If necessary and desired, the culture can be aerated or agitated.

When insect cells are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary and desired, the culture can be aerated or agitated.

When animal cells are employed as the host, the transformant is cultivated in, for example, MEM medium containing about 5% to about 20% fetal bovine serum (Science, 122, 501 (1952)), DMEM medium (Virology, 8, 396 (1959)), RPMI 1640 medium (The Journal of the American Medical Association, 199, 519 (1967)), 199 medium (Proceeding of the Society for the Biological Medicine, 73, 1 (1950)), etc. Preferably, pH of the medium is adjusted to about 6 to about 8. The transformant is usually cultivated at about 30° C. to about 40° C. for about 15 hours to about 72 hours and, if necessary and desired, the culture can be aerated or agitated.

When using CHO (dhfr⁻) cells and dhfr gene as a selection marker, thymidine-free DMEM medium containing dialyzed fetal bovine serum is preferred.

The mutein of the present invention can be separated and purified from the culture described above by the following procedures.

When the mutein of the present invention is extracted from the culture of bacteria or cells, after the culture of bacteria or cells are collected by a publicly known method and suspended in a appropriate buffer. The bacteria or cells are then disrupted by publicly known methods such as ultrasonication, a treatment with lysozyme and/or freeze-thaw cycling, followed by centrifugation, filtration, etc. Thus, the crude extract of the mutein of the present invention can be obtained. The buffer used for the procedure may contain a protein denaturing agent such as urea or guanidine hydrochloride, or a surfactant such as Triton X-100™, etc.

When the protein is secreted into the culture medium, after completion of the cultivation, the supernatant can be separated from the bacteria or cells to collect the supernatant by a publicly known method.

The mutein contained in the supernatant or the extract thus obtained can be purified by appropriately combining the publicly known methods for separation and purification. Such publicly known methods for separation and purification include a method utilizing difference in solubility such as salting out, solvent precipitation, etc.; a method utilizing mainly difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the mutein thus obtained is in a free form, it can be converted into a salt form by a publicly known method or modification thereof. On the other hand, when the mutein is obtained in a salt form, it can be converted into a free form or another salt form by a publicly known method or modification thereof.

The mutein produced by the recombinant can be treated, before or after the purification, with an appropriate protein-modifying enzyme so that the mutein can be appropriately modified or deprived of a partial polypeptide. Examples of the protein-modifying enzyme include trypsin, chymotrypsin, arginyl endopeptidase, protein kinase, glycosidase or the like.

The presence of the thus produced mutein of the present invention can be determined by an enzyme immunoassay using a specific antibody, or the like.

Neutralizing antibodies to MCP-1 (referred to as the antibodies of the present invention) may be any of polyclonal antibodies and monoclonal antibodies which are capable of neutralizing MCP-1 and recognizing MCP-1.

The antibodies of the present invention may be manufactured by a publicly known method for manufacturing antibodies or antisera, using MCP-1 as an antigen.

[Preparation of Monoclonal Antibody]

(a) Preparation of Monoclonal Antibody-producing Cells

MCP-1 is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once in every 2 to 6 weeks and 2 to 10 times in total. Examples of the applicable warm-blooded animals are monkeys, rabbits, dogs, guinea pigs, mice, rats, sheep and goats, chicken with mice and rats being preferred.

In the preparation of monoclonal antibody-producing cells, warm-blooded animals, e.g., mice are immunized with an antigen, the individual, in which the antibody titer is detected, is selected, then the spleen or lymph node is collected after 2 to 5 days from the final immunization. Antibody-producing cells contained therein are fused with myeloma cells to give monoclonal antibody-producing hybridomas. Measurement of the antibody titer in antisera may be made, for example, by reacting a labeled form of the protein, which will be described later, with the antiserum followed by assaying the binding activity of the labeling agent bound to the antibody. The fusion may be carried out by a known method, for example, by Koehler and Milstein method (Nature, 256 495, 1975). Examples of the fusion accelerator are polyethylene glycol (PEG), Sendai virus, etc., of which PEG is preferably employed.

Examples of the myeloma cells are NS-1, P3U1, SP2/0, AP-1, etc., i.e. ones derived from warm-blooded animals. In particular, P3U1 is preferably employed. A preferred ratio of the count of the antibody-producing cells used (spleen cells) to the count of myeloma cells is within a range of approximately 1:1 to 20:1. PEG (preferably, PEG 1000 to PEG 6000) may be added in a concentration of approximately 10 to 80%. An efficient cell fusion can be carried out by incubating at 20 to 40° C., preferably at 30 to 37° C. for 1 to 10 minutes.

Various methods can be used for screening of a monoclonal antibody-producing hybridoma. Examples of such methods include a method which comprises adding the supernatant of hybridoma to a solid phase (e.g., microplate) adsorbed with the protein as an antigen directly or together with a carrier, adding an anti-immunoglobulin antibody (when mouse cells are used for the cell fusion, anti-mouse immunoglobulin antibody is used) labeled with a radioactive substance or an enzyme, or Protein A and detecting the monoclonal antibody bound to the solid phase, and a method which comprises adding the supernatant of hybridoma to a solid phase adsorbed with an anti-immunoglobulin antibody or Protein A, adding the protein labeled with a radioactive substance or an enzyme and detecting the monoclonal antibody bound to the solid phase.

The monoclonal antibody can be selected by publicly known methods or by modifications of these methods. In general, the selection can be effected in a medium for animal cells supplemented with HAT (hypoxanthine, aminopterin and thymidine). Any selection and growth medium can be employed as far as the hybridoma can grow therein. For example, RPMI 1640 medium containing 1% to 20%, preferably 10% to 20% fetal bovine serum, GIT medium (Wako Pure Chemical Industries, Ltd.) containing 1% to 10% fetal bovine serum, a serum free medium for cultivation of a hybridoma (SFM-101, Nissui Seiyaku Co., Ltd.) and the like can be used for the selection and growth medium. The cultivation is carried out generally at 20° C. to 40° C., preferably at about 37° C., for 5 days to 3 weeks, preferably 1 to 2 weeks. The cultivation can be conducted normally in 5% $CO_2$. The antibody titer of the culture supernatant of hybridomas can be determined as in the assay for the antibody titer in antisera described above.

(b) Purification of Monoclonal Antibody

Separation and purification of a monoclonal antibody can be carried out by a known method, for example, according to a method for separation and purification of immunoglobulins [e.g., salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A, Protein G, etc. and dissociating the binding to obtain the antibody].

[Preparation of Polyclonal Antibody]

The polyclonal antibody of the present invention can be manufactured by a publicly known method or modification thereof. For example, a complex of immunogen (a protein antigen) and a carrier protein is prepared, and a warm-blooded animal is immunized with the complex in a manner similar to the method described above for the manufacture of monoclonal antibodies. A material containing the polyclonal antibody is collected from the immunized animal, and then separation and purification of the antibody are performed.

In the complex of an immunogen and a carrier protein used to immunize a warm-blooded animal, the type of carrier protein and the mixing ratio of a carrier to hapten may be any type and in any ratio, as long as the antibody is efficiently produced to the immunized hapten crosslinked to the carrier. For example, bovine serum albumin, bovine thyroglobulins, keyhole limpet hemocyanin, etc. is coupled to a hapten in a carrier-to-hapten weight ratio of about 0.1 to 20, preferably about 1 to 5.

A variety of condensing agents can be used for the coupling of a carrier to hapten. Glutaraldehyde, carbodiimide, maleimide activated ester, activated ester reagents containing thiol group or dithiopyridyl group, etc. are used for the coupling.

The condensation product is administered to warm-blooded animals either alone or together with a carrier or diluent to the site where the antibody-can be produce by the administration. In order to potentiate the antibody productivity upon the administration, complete Freund's adjuvant or incomplete Freund's adjuvant may be administered. The administration is usually made once approximately in every 2 to 6 weeks and about 3 to 10 times in total.

The polyclonal antibody can be collected from the blood, ascites, etc., preferably from the blood of warm-blooded animals immunized according to the method described above.

The polyclonal antibody titer in antiserum can be assayed by the same procedure as that for the determination of serum antibody titer described above. The separation and purification of the polyclonal antibody can be carried out, following the method for separation and purification of immunoglobulins as described in the separation and purification of the monoclonal antibodies.

The mutein of the present invention, the DNA encoding the mutein, or the antibody of the present invention can be used as a prophylactic and/or therapeutic agent for pulmonary hypertension, more specifically, primary pulmonary hypertension.

When the DNA encoding the mutein of the present invention is used as the prophylactic/therapeutic agent described above, the DNA is administered by itself; alternatively, the DNA is inserted into an appropriate vector such as retrovirus vector, adenovirus vector, adenovirus-associated virus vector, etc. and then administered in a conventional manner. The DNA of the present invention may also be administered as naked DNA or with an adjuvant to assist its uptake, by gene gun or through a catheter such as a catheter with a hydrogel.

When the mutein of the present invention is used as the prophylactic/therapeutic agent described above, the mutein may be used at purity level of at least 90%, preferably at least 95%, more preferably at least 98%, further preferably 99%.

When the mutein of the present invention or the antibody of the present invention is used as the prophylactic/therapeutic agent described above, it can be used orally, for example, in the form of tablet which may be sugar-coated if necessary and desired, capsule, elixir, microcapsule, etc., or parenterally in the form of injectable preparation such as a sterile solution and a suspension in water or with other pharmaceutically acceptable liquid. These preparations can be produced, for example, by mixing the mutein of the present invention with a physiologically acceptable carrier, a flavoring agent, an excipient, a vehicle, an antiseptic agent, a stabilizer, a binder, etc. in a unit dosage form which is generally accepted and required in a practical pharmaceutical preparation. The effective component in the preparation is adjusted to such a dose that an appropriate dose is obtained within the specified range.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of capsules, liquid carriers such as oils and fats may further be used together with the additives described above. A sterile composition for injection may be formulated by conventional procedures used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition. Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol and polyethylene glycol), a nonionic surfactant (e.g., polysorbate 80™ and HCO-50), etc. Examples of the oily medium include sesame oil and soybean oil, which may also be used in combination with a dissolution aid such as benzyl benzoate and benzyl alcohol. A buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. can also be formulated. The thus prepared liquid for injection is normally filled in an appropriate ampoule.

The vector as described above, into which the DNA of the present invention is incorporated, can also be formulated in the same was as described above, and usually used parenterally.

Since the thus obtained pharmaceutical preparations are safe and low toxic, the preparations can be administered to a human or mammal (e.g., rat, mouse, guinea pig, rabbit, sheep, swine, bovine, cat, dog, monkey, etc.).

The DNA encoding the mutein of the present invention, or the vector containing the DNA can be used for gene therapy for pulmonary hypertension (particularly, primary pulmonary hypertension).

The dose of the prophylactic/therapeutic agent of the present invention varies depending on disease to be targeted, subject to be administered, route for administration, etc. In case of administering the mutein, the DNA or the antibody of the present invention to an adult patient (60 kg body weight) with primary pulmonary hypertension in a form of injectable preparation, it is advantageous to administer the active ingredient intravenously in a daily dose of about 0.01 to 30 mg, preferably about 0.1 to 20 mg, and more preferably about 0.1 to 10 mg. For other animal species, the corresponding dose as converted per 60 kg body weight can be administered.

In the specification and drawings, abbreviations of bases and amino acids are based on the abbreviations of the IUPAC-IUB Commission on Biochemical Nomenclature or the conventional abbreviations used in the art, examples of which are shown below. An amino acid that has an optical isomer takes its L form unless otherwise indicated.

| | |
|---|---|
| DNA | deoxyribonucleic acid |
| cDNA | complementary deoxyribonucleic acid |
| A | adenine |
| T | thymine |
| G | guanine |
| C | cytosine |
| RNA | ribonucleic acid |
| mRNA | messenger ribonucleic acid |
| dATP | deoxyadenosine triphosphate |
| dTTP | deoxythymidine triphosphate |
| dGTP | deoxyguanosine triphosphate |
| dCTP | deoxycytidine triphosphate |
| ATP | adenosine triphosphate |
| EDTA | ethylenediaminetetraacetic acid |
| SDS | sodium dodecyl sulfate |
| Gly | glycine |
| Ala | alanine |
| Val | valine |
| Leu | leucine |
| Ile | isoleucine |
| Ser | serine |
| Thr | threonine |
| Cys | cysteine |
| Met | methionine |
| Glu | glutamic acid |
| Asp | aspartic acid |
| Lys | lysine |
| Arg | arginine |
| His | histidine |
| Phe | phenylalanine |
| Tyr | tyrosine |
| Trp | tryptophan |
| Pro | proline |
| Asn | asparagine |
| Gln | glutamine |
| pGlu | pyroglutamic acid |

The substituents, protective groups and reagents, which are frequently used throughout the specification, are shown by the following abbreviations.

| | |
|---|---|
| Me | methyl |
| Et | ethyl |
| Bu | butyl |
| Ph | phenyl |
| TC | thiazolidine-4(R)-carboxamide |
| Tos | p-toluenesulfonyl |
| CHO | formyl |
| Bzl | benzyl |
| Cl$_2$Bl | 2,6-dichlorobenzyl |
| Bom | benzyloxymethyl |
| Z | benzyloxycarbonyl |
| Cl-Z | 2-chlorobenzyloxycarbonyl |
| Br-Z | 2-bromobenzyloxycarbonyl |
| Boc | t-butoxycarbonyl |
| DNP | dinitrophenol |
| Trt | trityl |
| Bum | t-butoxymethyl |
| Fmoc | N-9-fluorenylmethoxycarbonyl |
| HOBt | 1-hydroxybenztriazole |
| HOOBt | 3,4-dihydro-3-hydroxy-4-oxo-1,2,3-benzotriazine |
| HONB | 1-hydroxy-5-norbornene-2,3-dicarboximide |
| DCC | N,N'-dicyclohexylcarbodiimide |

Each SEQ ID NO (sequence identification number) in the Sequence Listing of the specification indicates the following sequence, respectively.

[SEQ ID NO: 1]
This shows the amino acid sequence of MCP-1.
[SEQ ID NO: 2]
This shows the amino acid sequence of 7ND-MCP-1.
[SEQ ID NO: 3]
This shows the nucleic acid sequence of DNA encoding MCP-1.
[SEQ ID NO: 4]
This shows the nucleic acid sequence of DNA encoding 7ND-MCP-1.

The present invention is described more specificically with reference to the following examples, being not intended to limit the scope of the present invention thereto.

EXAMPLE 1

Effect of an antagonistic mutein of MCP-1 on the monocrotaline (MCT)-induced pulmonary hypertensive rat model.

Method: Normal rats (commercially available male rats with normal blood pressure (6-8 week old)) were divided into four groups. The first group is an untreated control group, the second group is an MCT (60 mg/kg, s.c.) treated control group, the third group is an MCT-treated group administered with a single dose of 7ND-MCP-1 (administered simultaneously with MCT-treatment), and the fourth group is an MCT-treated group administered with two doses of 7ND-MCP-1 (administered simultaneously with MCT-treatment and two weeks after the MCT-treatment). Three days before the gene introduction, 500 µl of marcaine was injected into the bilateral quadriceps femoris muscles of the rats, and three days later, 60 mg/kg MCT was subcutaneously injected into the MCT (60 mg/kg, s.c.) treated control group rats. To the rats in the group administered with a single dose of 7ND-MCP-1 were injected with 500 µg of 7ND-MCP-1 expressing plasmids in the several discrete sites in the bilateral quadriceps femoris muscles simultaneously with 60 mg/kg MCT. To the rats in the group administered with two doses of 7ND-MCP-1 were injected with 500 µg of 7ND-MCP-1 expressing plasmids in the several discrete sites in the bilateral quadriceps femoris muscles simultaneously with 60 mg/kg MCT, and 14 days later, the rats were injected with 500 µg of 7ND-MCP-1 expressing plasmids in the several discrete sites in the bilateral quadriceps femoris muscles. Changes in the morphology of the cardiac ventricles and lumen sizes were investigated by echocardiography and pressure in the right cardiac ventricles was determined 1, 2, 3 and 4 weeks after the MCT-treatment. Cardiac weight, thickness of the right cardiac ventricle walls and lumen size of the cardiac ventricles were measured for the hearts extirpated in the fourth week, and morphological analysis of the lungs was performed.

The 7ND-MCP-1 expression plasmid was generated as follows: 7ND-MCP-1 cDNA was obtained by PCR, a well-known technique in the art, using the MCP-1 cDNA as the template (FLAG sequence can be added to the 3' terminus of 7ND-MCP-1); and the 7ND-MCP-1 cDNA was inserted between the BamHI and NotI sites of the pCDNA3 expression plasmid such that the 5' terminus of the cDNA is located at the BamHI site and the 3' terminus is located at the NotI site.

The results are shown below.

1. Effect on Pulmonary Hypertension

While the pressure in the right cardiac ventricles was 26.2±4.7 mmHg in the untreated control group, it was increased to 69.7±2.1 mmHg four weeks after the MCT-treatment. However, it was decreased to 37.3±4.6 mmHg and 45.9±9.8 mmHg after the administration of a single dose and two doses of 7ND-MCP-1 (an antagonistic mutein of MCP-1), respectively, thus confirming a significant blood pressure lowering effect.

2. Effect on the Cardiac Weight and Morphological Changes in the Heart

While right ventricular hypertrophy, particularly increase of thickness of the right cardiac ventricle walls, and lumen enlargement were observed in the MCT-treated group, these changes were prevented by administration of 7ND-MCP-1.

3. Effect on Blood Vessels and Lung

Although significant hypertrophy of the tunica media was observed in the arterioles of the right cardiac ventricles in the MCT-administered group, this change was suppressed by administration of 7ND-MCP-1. While infiltration of large number of monocytes and macrophages predominantly in the alveolar space was also observed in the MCT-treated group, these changes were suppressed by administration of 7ND-MCP-1.

In view of the effect of 7ND-MCP-1 administration on monocrotaline (MCT)-induced pulmonary hypertension and remodeling of pulmonary artery and cardiac ventricle walls developing in association with the hypertension in the rats, an antagonistic mutein of MCP-1 is thought to be a potential prophylactic or therapeutic agent for pulmonary hypertension (primary pulmonary hypertension, in particular).

INDUSTRIAL APPLICABILITY

An agent comprising the antagonistic mutein of MCP-1 of the present invention, the DNA molecule having a nucleotide sequence encoding the antagonistic mutein of MCP-1, or the neutralizing antibody against MCP-1 is useful as a pharmaceutical agent for preventing or treating pulmonary hypertension (primary pulmonary hypertension, in particular).

The invention claimed is:

1. A method for treating pulmonary hypertension, comprising intramuscular administration of an effective amount of an nucleic acid encoding for a protein having the amino acid sequence of SEQ ID NO.: 2, or of a vector comprising said nucleic acid, to a mammal exhibiting pulmonary hypertension, wherein expression of the nucleic acid results in reduced blood pressure in said mammal.

2. The method of claim 1 wherein said nucleic acid is DNA.

3. The method of claim 1 wherein said vector is a plasmid vector.

4. The method of claim 1 wherein said vector is a viral vector.

* * * * *

SEQUENCE LISTING

<160> NUMBER OF SEQ ID NOS: 4

<210> SEQ ID NO 1
<211> LENGTH: 76
<212> TYPE: PRT
<213> ORGANISM: Human

<400> SEQUENCE: 1

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75

<210> SEQ ID NO 2
<211> LENGTH: 69
<212> TYPE: PRT
<213> ORGANISM: Human

<400> SEQUENCE: 2

Gln Val Thr Cys Cys Tyr Asn Phe Thr Asn Arg Lys Ile Ser Val Gln
1               5                   10                  15

Arg Leu Ala Ser Tyr Arg Arg Ile Thr Ser Ser Lys Cys Pro Lys Glu
            20                  25                  30

```
Ala Val Ile Phe Lys Thr Ile Val Ala Lys Glu Ile Cys Ala Asp Pro
        35                  40                  45

Lys Gln Lys Trp Val Gln Asp Ser Met Asp His Leu Asp Lys Gln Thr
    50                  55                  60

Gln Thr Pro Lys Thr
65

<210> SEQ ID NO 3
<211> LENGTH: 228
<212> TYPE: DNA
<213> ORGANISM: Human

<400> SEQUENCE: 3
cagccagatg caatcaatgc cccagtcacc tgctgttata acttcaccaa taggaagatc      60
tcagtgcaga ggctcgcgag ctatagaaga atcaccagca gcaagtgtcc caaagaagct    120
gtgatcttca agaccattgt ggccaaggag atctgtgctg accccaagca gaagtgggtt    180
caggattcca tggaccacct ggacaagcaa acccaaactc cgaagact                 228

<210> SEQ ID NO 4
<211> LENGTH: 207
<212> TYPE: DNA
<213> ORGANISM: Human

<400> SEQUENCE: 4
caggtcacct gctgttataa cttcaccaat aggaagatct cagtgcagag gctcgcgagc     60
tatagaagaa tcaccagcag caagtgtccc aaagaagctg tgatcttcaa gaccattgtg    120
gccaaggaga tctgtgctga ccccaagcag aagtgggttc aggattccat ggaccacctg    180
gacaagcaaa cccaaactcc gaagact                                        207
```